US 7,851,444 B2

(12) United States Patent
Lewis et al.

(10) Patent No.: US 7,851,444 B2
(45) Date of Patent: *Dec. 14, 2010

(54) χ-CONOTOXIN PEPTIDES (-1)

(75) Inventors: Richard James Lewis, Woolloongabba (AU); Paul Francis Alewood, Pullenvale (AU); Dianne Alewood, Pullenvale (AU); Elka Palant, Kenmore (AU)

(73) Assignee: Xenome Ltd., Queenslamd (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/537,704

(22) PCT Filed: Dec. 2, 2003

(86) PCT No.: PCT/AU03/01605

§ 371 (c)(1),
(2), (4) Date: Dec. 12, 2005

(87) PCT Pub. No.: WO2004/050690

PCT Pub. Date: Jun. 17, 2004

(65) Prior Publication Data

US 2006/0142201 A1 Jun. 29, 2006

Related U.S. Application Data

(60) Provisional application No. 60/430,306, filed on Dec. 2, 2002.

(51) Int. Cl.
*A61K 38/00* (2006.01)
*A61K 38/04* (2006.01)
*A61K 51/00* (2006.01)

(52) U.S. Cl. .............................. 514/14; 514/2; 530/327; 424/1.69

(58) Field of Classification Search ........................ None
See application file for complete search history.

(56) References Cited

U.S. PATENT DOCUMENTS

| 5,587,454 A | 12/1996 | Justice et al. | |
|---|---|---|---|
| 6,767,896 B1* | 7/2004 | McIntosh et al. | 514/14 |
| 6,794,361 B1 | 9/2004 | Lewis et al. | |
| 7,326,682 B2 | 2/2008 | Lewis et al. | |
| 2003/0170222 A1* | 9/2003 | Jones et al. | 424/94.1 |
| 2004/0176278 A1* | 9/2004 | Jones et al. | 514/7 |
| 2005/0054827 A1 | 3/2005 | Lewis et al. | |
| 2005/0271589 A1* | 12/2005 | Jones et al. | 424/1.69 |
| 2009/0088389 A1 | 4/2009 | Lewis et al. | |
| 2009/0275498 A1 | 11/2009 | Lewis et al. | |

FOREIGN PATENT DOCUMENTS

| WO | WO 91/07980 | 6/1991 |
|---|---|---|
| WO | WO 96/14079 | 5/1996 |
| WO | WO 96/40064 | 12/1996 |
| WO | WO 97/01351 | 1/1997 |
| WO | WO 97/30997 | 8/1997 |
| WO | WO 98/02148 | 1/1998 |
| WO | WO 98/05309 | 2/1998 |
| WO | WO 98/22126 | 5/1998 |
| WO | WO 98/51668 | 11/1998 |
| WO | WO 00/20444 | 4/2000 |
| WO | WO 00/44769 | 8/2000 |

OTHER PUBLICATIONS

Balaji et al. 2000, J. Biol. Chem. 275(50): 39516-39522.*
Bowersox, S.S. et al., "Selective N-Type Neuronal Voltage-Sensitive Calcium Channel Blocker, SNX-111, Produces Spinal Antinociception in rat Models of Acute, Persistent and Neuropathic Pain", J. Pharmacol Exp. Ther., 279 (3): 1243-1249 (1996).
Krames, Elliot S. et al., "Intrathecal D-Ala2-D-Leu5-enkephalin (DADL) Restores Analgesia in a Patient Analgetically Tolerant to Intrathecal Morphine Sulfate", Pain, 24: 205-209 (1986).
Takagi, H. et al., "Analgesic Effect of L-threo-3-4-dihydroxyphenylserine (L-DOPS) in Patients with Chronic Pain", European Neuropsychopharmacology, 6: 43-47 (1996).
Eisenach, C. et al., "Cerebrospinal Fluid Norepinephrine and Acetylcholine Concentrations During Acute Pain", Anesth Analg, 82: 621-626 (1996).
Dubner, R. et al., "The Neurobiology of Pain and Its Modulation", The Clinical Journal of Pain, 5(Suppl 2): S1-S6 (1989).
Dyck, P.J et al., "New Understanding and Treatment of Diabetic Neuropathy", The New England Journal of Medicine, 326(19):1287-1288(1992).
Atkinson, J. H. et al., "A Placebo-controlled Randomized Clinical Trial of Nortriptyline for Chronic Low Back Pain", Pain, 76: 287-296 (1998).
Mico, J. A., et al., "Analgesic, Sedative and Antidepressant Effects of Noradrenergic Antidepressants Related to Beta-Adrenoceptors", European Neuropsychopharmacology, S162, p. 1.086, Abstract (1997).
Springer, J. P. et al., "Facilitatory and Inhibitory Effects of Selective Norephinephrine Reuptake Inhibitors on Hypogastric Nerve-Evoked Urethral Contractions in the Cat: A Prominent Role of Urethral S-Adrenergic Receptors", The Journal of Urology, 152: 515-519 (1984).
Diann, T. G. et al., "Assessment of Central Noradrenergic Functioning in Irritable Bowel Syndrome Using a Neuroendocrine Challenge Test", Journal of Psychosomatic Research, 34(5): 575-580 (1990).

(Continued)

*Primary Examiner*—Maury Audet
(74) *Attorney, Agent, or Firm*—Schully, Scott, Murphy & Presser, P.C.

(57) ABSTRACT

An isolated, synthetic or recombinant χ-conotoxin peptide comprising the following sequence of amino acids: Xaa1 Xaa2 Gly Val Cys Cys Gly Tyr Lys Leu Cys His Pro Cys SEQ ID NO. 3 where Xaa1 is a N-terminal Xaa1 is a N-terminal pyroglutamate (pGlu) or D-pyroglutamate (DpGlu) residue; and Xaa2 is Asn or a deletion; or such a sequence in which one or more Cys is replaced with its corresponding D-amino acid and/or one or more amino acid residues other than Cys has undergone a side chain modification, or a salt, ester, amide or prodrug thereof. The invention also relates to pharmaceutical compositions comprising these peptides and the use of these peptides in the prophylaxis or treatment of conditions, such as but not limited to, pain, inflammation, incontinence, cardiovascular conditions and mood disorders.

13 Claims, 2 Drawing Sheets

OTHER PUBLICATIONS

Figure 1:
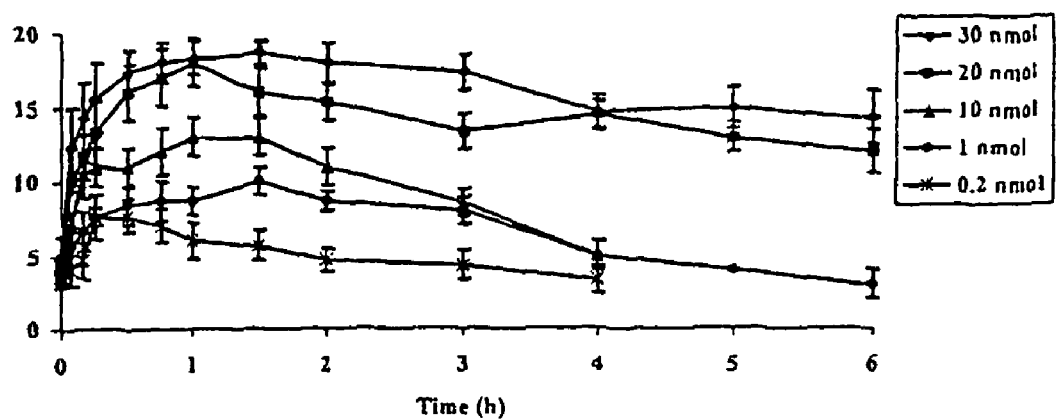
Figure 1:
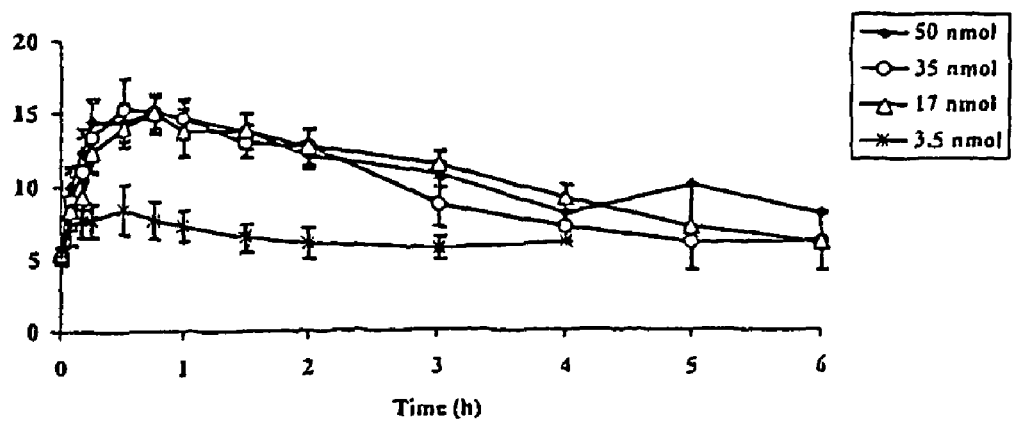
Figure 1:
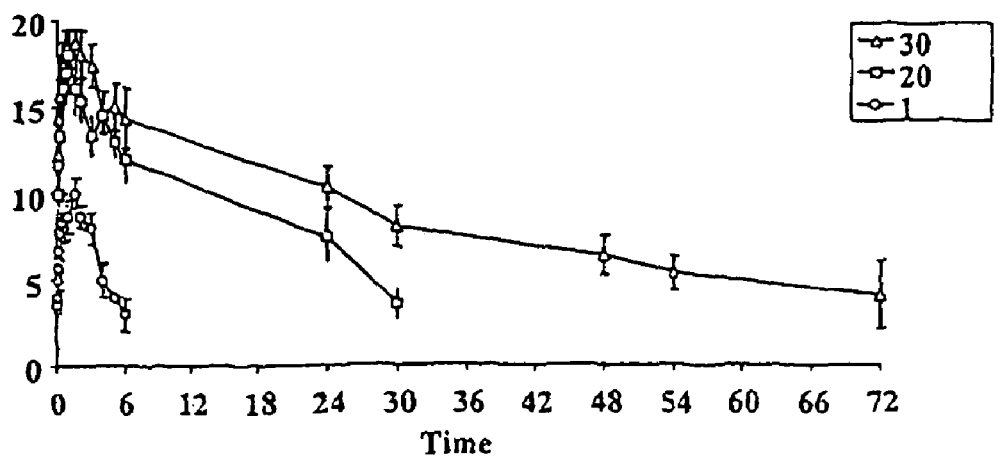

Leung, D. et al., "Protease Inhibitors: Current Status and Future Prospects", J. Med Chem, 43(3): 305-341 (2000).

O'Neill, M. J. et al., "Effects of Ca2+ and Na+ channel inhibitors in vitro and inn global cerebal ischaemia in vivo", European Journal of Pharmacology, 332: 121-131 (1997).

Eisenach, J. C. et al., "Intrathecal, but Not Intravenous, Clonidine Reduces Experimental Thermal or Capsaicin-Induced Pain and Hyperalgesia in Normal Volunteers", Anesth Analg, 87:591-596 (1998).

Marban, E. et al., "Structure and Function of Voltage-Gated Sodium Channels", Journal of Physiology, 508.3: 647-657 (1998).

Yanagawa, Y. et al., "A Novel Sodium Channel Inhibitor from Conus geographus: Purification, Structure, and Pharmacological Properties", Biochemistry, 27: 6256-6262 (1988).

Ryan, R., et al., "Evaluation of an Enkephalin Analog in Men with Castor Oil-Induced Diarrhea", Clinical Pharmacol Ther, 39(1): 40-42 (1986).

Penttila, O, et al., "Studies of Rectal Mucosal Catecholamines in Ulcerative Colitis", Annals of Clinical Research, 7: 32-36 (1975).

* cited by examiner a)

b)

c)

SEQUENCE LISTING

```
<160> NUMBER OF SEQ ID NOS: 12

<210> SEQ ID NO 1
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: X is 4-hydroxyproline
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 1

Asn Gly Val Cys Cys Gly Tyr Lys Leu Cys His Xaa Cys
1               5                   10

<210> SEQ ID NO 2
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: X is 4-hydroxyproline
```

```
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 2

Val Gly Val Cys Cys Gly Tyr Lys Leu Cys His Xaa Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is a pGLU or DpGlu residue
<220> FEATURE:
<221> NAME/KEY: MISC_FEATURE
<222> LOCATION: (2)..(2)
<223> OTHER INFORMATION: X is Asn or a deletion
<220> FEATURE:
<221> NAME/KEY: DISULFID
<222> LOCATION: (5)..(14)
<223> OTHER INFORMATION:
<220> FEATURE:
<221> NAME/KEY: DISULFID
<222> LOCATION: (6)..(11)
<223> OTHER INFORMATION:

<400> SEQUENCE: 3

Xaa Xaa Gly Val Cys Cys Gly Tyr Lys Leu Cys His Pro Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: MOD_RES
<222> LOCATION: (13)..(13)
<223> OTHER INFORMATION: AMIDATION
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 4

Xaa Gly Val Cys Cys Gly Tyr Lys Leu Cys His Xaa Cys
1               5                   10
```

```
<210> SEQ ID NO 5
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: misc_feature
<222> LOCATION: (13)..(13)
<223> OTHER INFORMATION: X is D-cysteine
<220> FEATURE:
<221> NAME/KEY: MOD_RES
<222> LOCATION: (13)..(13)
<223> OTHER INFORMATION: AMIDATION
<220> FEATURE:
<221> NAME/KEY: DISULFID
<222> LOCATION: (5)..(10)
<223> OTHER INFORMATION:

<400> SEQUENCE: 5

Xaa Gly Val Cys Cys Gly Tyr Lys Leu Cys His Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (7)..(7)
<223> OTHER INFORMATION: X is 4-methoxytyrosine
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:
<220> FEATURE:
<221> NAME/KEY: MOD_RES
<222> LOCATION: (13)..(13)
<223> OTHER INFORMATION: AMIDATION

<400> SEQUENCE: 6

Xaa Gly Val Cys Cys Gly Xaa Lys Leu Cys His Xaa Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (8)..(8)
<223> OTHER INFORMATION: X is 4-methoxytyrosine
<220> FEATURE:
<221> NAME/KEY: misc_feature
<222> LOCATION: (13)..(13)
<223> OTHER INFORMATION: X is 4-hydroxyproline
<220> FEATURE:
<221> NAME/KEY: MOD_RES
<222> LOCATION: (13)..(13)
<223> OTHER INFORMATION: AMIDATION
<220> FEATURE:
<221> NAME/KEY: DISULFID
<222> LOCATION: (5)..(14)
<223> OTHER INFORMATION:
<220> FEATURE:
<221> NAME/KEY: DISULFID
<222> LOCATION: (6)..(11)
<223> OTHER INFORMATION:

<400> SEQUENCE: 7

Xaa Asn Gly Val Cys Cys Gly Xaa Lys Leu Cys His Xaa Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (13)..(13)
<223> OTHER INFORMATION: X is 4-hydroxyproline
<220> FEATURE:
<221> NAME/KEY: MOD_RES
<222> LOCATION: (13)..(13)
<223> OTHER INFORMATION: AMIDATION
<220> FEATURE:
<221> NAME/KEY: DISULFID
<222> LOCATION: (5)..(14)
<223> OTHER INFORMATION:
<220> FEATURE:
<221> NAME/KEY: DISULFID
<222> LOCATION: (6)..(11)
<223> OTHER INFORMATION:

<400> SEQUENCE: 8

Xaa Asn Gly Val Cys Cys Gly Tyr Lys Leu Cys His Xaa Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamic acid
<220> FEATURE:
<221> NAME/KEY: misc_feature
<222> LOCATION: (12)..(12)
<223> OTHER INFORMATION: X is 4-hydroxyproline
```

```
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 9

Xaa Gly Val Cys Cys Gly Tyr Lys Leu Cys His Xaa Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is D-pyroglutamic acid
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 10

Xaa Gly Val Cys Cys Gly Tyr Lys Leu Cys His Xaa Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is D-pyroglutamic acid
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: MOD_RES
<222> LOCATION: (13)..(13)
<223> OTHER INFORMATION: AMIDATION
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 11

Xaa Gly Val Cys Cys Gly Tyr Lys Leu Cys His Xaa Cys
1               5                   10
```

```
<210> SEQ ID NO 12
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: X is pyroglutamate
<220> FEATURE:
<221> NAME/KEY: misc_feature
<222> LOCATION: (11)..(11)
<223> OTHER INFORMATION: X is D-histidine
<220> FEATURE:
<221> NAME/KEY: misc_feature
<222> LOCATION: (12)..(12)
<223> OTHER INFORMATION: X is 4-hydroxyproline
<220> FEATURE:
<221> NAME/KEY: MOD_RES
<222> LOCATION: (1)..(1)
<223> OTHER INFORMATION: AMIDATION
<220> FEATURE:
<221> NAME/KEY: DISULFID
<222> LOCATION: (4)..(13)
<223> OTHER INFORMATION:
<220> FEATURE:
<221> NAME/KEY: DISULFID
<222> LOCATION: (5)..(10)
<223> OTHER INFORMATION:

<400> SEQUENCE: 12

Xaa Gly Val Cys Cys Gly Tyr Lys Leu Cys Xaa Xaa Cys
1               5                  10
```

χ-CONOTOXIN PEPTIDES (-1)

CROSS REFERENCE TO RELATED APPLICATIONS

This application is the §371 national phase of PCT/AU2003/001605, filed on Dec. 2, 2003, which claims priority from U.S. Provisional Application No. 60/430,306, filed on Dec. 2, 2002.

The present invention relates to novel χ-conotoxin peptides useful as inhibitors of neuronal amine transporters of neurotransmitters such as noradrenaline, serotonin, dopamine, glutamic acid and glycine. The invention also relates to pharmaceutical compositions comprising these peptides and the use of these peptides in the prophylaxis or treatment of conditions, such as but not limited to, pain, inflammation, incontinence, cardiovascular conditions and mood disorders.

The marine snails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. The venom from any single *Conus* species may contain more than 100 different peptides. The conotoxins are divided into classes on the basis of their physiological targets. The ω-conotoxin class of peptides target and block voltage-sensitive $Ca^{2+}$-channels inhibiting neurotransmitter release. The α-conotoxins and ψ-conotoxins target and block nicotinic ACh receptors, causing ganglionic and neuromuscular blockade. Peptides of the μ-conotoxin class act to block voltage-sensitive $Na^+$-channels inhibiting muscle and nerve action potentials. The δ-conotoxins target and delay the inactivation of voltage-sensitive $Na^+$-channels, enhancing neuronal excitability. The κ-conotoxin class of peptides target and block voltage-sensitive $K^+$-channels, and these also cause enhanced neuronal excitability. The conopressins are vasopressin receptor antagonists and the conantokins are NMDA receptor antagonists. The γ-conotoxin class targets a voltage-sensitive nonspecific cation channel. The σ-conotoxin class antagonises the $5HT_3$ receptor and the χ-conotoxin class inhibits neuronal amine transporters.

The χ-conotoxin class of peptides was first described in WO00/20444 (University of Queensland), although two members of the class were subsequently referred to in WO00/44769 (University of Utah Research Foundation). The particular χ-conotoxin peptide identified WO 00/20444 were MrIA and MrIB from mollusc hunting *C. marmoreus* which have the following sequences:

```
χ-MrIA Asn Gly Val Cys Cys Gly Tyr Lys SEQ ID NO. 1
      Leu Cys His Xaa3 Cys

χ-MrIB Val Gly Val Cys Cys Gly Tyr Lys SEQ ID NO. 2
      Leu Cys His Xaa3 Cys
```

In these and following sequences the Xaa3 refers to 4-hydroxy proline (Hyp). In nature, this amino acid residue results from post translational modification of the encoded peptide and is not directly encoded by the nucleotide sequence.

Compounds which inhibit neurotransmitter reuptake have been found to be useful in the treatment of acute, chronic and/or neuropathic pain, migraine or inflammation. Such compounds can also be administered with other agents useful in these treatments to provide improved pain/inflammation relief and/or reduce the severity of unwanted side effects, such as nausea and stomach upset. They have also been found to be useful in the treatment of lower urinary tract disorders, such as urinary incontinence, detrusor instability and interstitial cystitis. One such compound is "imipramine" which, in addition to inhibiting noradrenaline reuptake, has been shown to affect calcium channel blockade, and to exhibit anticholinergic, local anaesthetic activity and a number of other effects. Other compounds capable of inhibiting noradrenaline reuptake are described in U.S. Pat. No. 5,441,985. These compounds are said to have a reduced anticholinergic effect relative to imipramine.

In the case of the peptides of the present invention this inhibition of neurotransmitter reuptake is achieved by selectively inhibiting the neuronal neurotransmitter transporter, such as the noradrenaline transporter, which functions to rapidly clear released noradrenaline from the synapse back into neurons.

As described in WO00/20444, the peptide χ-MrIA is composed of a tail, residues 1-3, two loops, residues 6-9 (loop 1) and 11-12 (loop 2), respectively and have two disulfide bonds between cysteine residues 4 and 13 and 5 and 10, respectively. While MrIA resembles a α-conotoxin peptide in terms of the number of cysteine residues, the disulfide connectivity is different. In this regard the α-conotoxin peptides are characterised by an A-C/B-D connectivity, rather than the A-D/B-C connectivity of MrIA, where A, B, C and D represent the first, second, third and fourth cysteine residues involved in disulfide bond formation, respectively.

It has now been surprisingly found that the substitution of the N-terminal asparagine residue of MrIA with a pyroglutamic acid residue or the addition a pyroglutamate residue to the N-terminus of MrIA provides particular advantages over MrIA in terms of in vivo efficacy, duration of effect, stability and method of preparation.

Accordingly in a first aspect the present invention there is provided an isolated, synthetic or recombinant χ-conotoxin peptide comprising the following sequence of amino acids:

```
Xaa1 Xaa2 Gly Val Cys Cys Gly Tyr Lys SEQ ID NO. 3
Leu Cys His Pro Cys
``` where Xaa1 is a N-terminal pGlu or DpGlu residue; and

Xaa2 is Asn or a deletion;

or such a sequence in which one or more Cys is replaced with its corresponding D-amino acid and/or one or more amino acid residues other than Cys has undergone a side chain modification, or a salt, ester, amide or prodrug thereof.

In a second aspect the present invention provides an isolated, synthetic or recombinant χ-conotoxin peptide consisting of the following sequence of amino acids:

```
Xaa1 Xaa2 Gly Val Cys Cys Gly Tyr Lys SEQ ID NO. 3
Leu Cys His Pro Cys
``` where Xaa1 is a N-terminal pGlu or DpGlu residue; and

Xaa2 is Asn or a deletion, or such a sequence in which one or more Cys is replaced with its corresponding D-amino acid and/or one or more amino acid residues other than Cys has undergone a side chain modification, or a salt, ester, amide or prodrug thereof.

In the above sequences pGlu represents pyroglutamate and DpGlu represents D-pyroglutamate.

The peptides according to the present invention have a number of surprising and unexpected advantages over MrIA. The peptides have also been found to be particularly stable to storage in the pH range of 4 to 7 and 37 EC, allowing long term delivery in a device, for example an infusion pump, held at room temperature to 37 EC. There are also advantages in relation to the production and separation of the peptides from unwanted bi-products of synthesis, allowing straightforward purification to homogeneity of >99%, relative to MrIA using a similar procedure in which purity is typically <93%. When delivered i.t. in a rat neuropathic model of allodynia, a peptide according to the present invention was found to have greater maximum efficacy relative to MrIA, without influencing the side effects or reducing the therapeutic window in the animal model. The duration of effect of the peptide was found to extend beyond 48 hours following a bolus 30 nmol dose given i.t. The peptides according to the present invention are particularly useful in the treatment of neuropathic pain and its symptoms when delivered in an appropriate buffer i.t. or epidural. Such neuropathic pain conditions including surgery (post operative pain), gut, cancer, diabetic, phantom limb, nerve damage, inflammatory pain and peripheral nerve associated pain.

Preferably, the neuronal amine transporter inhibited by the χ-conotoxin peptide is the neuronal noradrenaline transporter.

The χ-conotoxin peptide may be naturally occurring peptides isolated from a cone snail, or derivatives or synthetic versions thereof.

Preferably, the χ-conotoxin peptide is a selective inhibitor of the neuronal noradrenaline transporter. The terms "selective" and "selectively" as used herein mean that the activity of the peptide as an inhibitor of neuronal noradrenaline transporter is considerably greater than any activity at the $\alpha_1$-adrenoceptors. Preferably the peptide inhibitor is 10-fold more selective towards the neuronal noradrenaline transporter, more preferably 100-fold more selective and most preferably more than 1000-fold more selective. The peptide is also preferably selective over $\alpha_2$-adrenoceptors and/or serotonin reuptake transporter (SERT). The selectivity of an inhibitor of the neuronal noradrenaline transporter can be measured using techniques known in the art, for example using appropriate labelled ligand displacement assays.

U.S. Pat. No. 5,441,985 indicates that inhibitors of noradrenaline reuptake which have a negligible anticholinergic effect are particularly useful in the treatment of lower urinary tract disorders. It has been found that the peptides of this invention also have no detectable or substantially no detectable anticholinergic effect.

Accordingly in a preferred embodiment of the invention the χ-conotoxin peptide has the ability to selectively inhibit neuronal noradrenaline transporter, and has negligible or no substantial anticholinergic effect.

The peptides of the present invention preferably have no activity as a sodium channel blocker or as an inhibitor of dopamine transporter. The absence, in the peptides of the invention and in particular the preferred peptides according to the invention, of these additional pharmacological activities commonly associated with other noradrenaline transporter inhibitors makes these peptides useful pharmacological tools.

The peptides according to the present invention are specific derivatives of MrIA.

The term "derivative" as used herein in connection with a naturally occurring χ-conotoxin peptide, such as χ-MrIA, refers to a peptide which differs from the naturally occurring peptides by one or more amino acid deletions, additions, substitutions; or side-chain modifications. All such derivatives according to the present invention have the ability to inhibit neuronal noradrenaline transporter.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example Lys residues may be substituted by ornithine, homoarginine, nor-Lys, N-methyl-Lys, N,N-dimethyl-Lys and N,N,N-trimethyl-Lys. Lys residues can also be replaced with synthetic basic amino acids including, but not limited to, N-1-(2-pyrazolinyl)-Arg, 2-(4-piperinyl)-Gly, 2-(4-piperinyl)-Ala, 2-[3-(2S)pyrrolininyl]-Gly and 2-[3-(2S)pyrolininyl]-Ala. Tyr residues may be substituted with 4-methoxy tyrosine (MeY), meta-Tyr, ortho-Tyr, nor-Tyr, $^{125}$I-Tyr, mono-halo-Tyr, di-halo-Tyr, O-sulpho-Tyr, O-phospho-Tyr, and nitro-Tyr. Tyr residues may also be substituted with the 3-hydroxyl or 2-hydroxyl isomers, (meta-Tyr or ortho-Tyr, respectively) and corresponding O-sulpho- and O-phospho derivatives. Tyr residues can also be replaced with synthetic hydroxyl containing amino acids including, but not limited to 4-hydroxymethyl-Phe, 4-hydroxyphenyl-Gly, 2,6-dimethyl-Tyr and 5-amino-Tyr. Aliphatic amino acids may be substituted by synthetic derivatives bearing non-natural aliphatic branched or linear side chains $C_nH_{2n+2}$ up to and including n=8. Examples of suitable conservative substitutions by non-conventional amino acids are given in WO02/064740, the entire contents of which is incorporated herein by reference. According to the present invention substitutions are restricted to conservative substitutions.

Amino acid substitutions are typically of single residues, but may be of multiple residues, either clustered or dispersed.

Additions encompass the addition of one or more naturally occurring or non-conventional amino acid residues. Peptides according to the present invention where Xaa2 is Asn may be considered derivatives of MrIA having an additional Xaa1 residue. Other additions are restricted to the C-terminus. Deletion encompasses the deletion of one or more amino acid residues.

As stated above the present invention includes peptides in which one or more of the amino acids other than Cys has undergone sidechain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$; and N-acetylation.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Acidic amino acids may be substituted with tetrazolyl derivatives of glycine and alanine, as described in WO02/600923.

The tyrosine residue may be altered, for example by methoxylation at the 4-position. Tyrosine may also be altered by nitration with tetranitromethane to form a 3-nitrotyrosine derivative. Examples of tyrosine derivatives are given in WO02/064740.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

Other derivatives contemplated by the present invention include a range of glycosylation variants. Altered glycosylation patterns may result from expression of recombinant molecules in different host cells. Ser, Thr and Hyp residues may be modified to contain an O-glycan, while Asn and Gln residues can be modified to form a N-glycan. In accordance with the present invention, the term "glycan" refers to an N-, S- or O-linked mono-, di-, tri, poly- or oligosaccharide that can be attached to any hydroxy, amino or thiol group of natural of modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNac), D-fucose or D-arabinose. These saccharides may be structurally modified ie., with one or more O-sulphate, O-phosphate, O-acetyl or acidic groups such as sialic acid, including combinations thereof. The glycan may also include similar polyhydroxyl groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1.

A list of some amino acids having modified side chains and other unnatural amino acids is shown in Table 1.

TABLE 1

| Non-conventional amino acid | Code | Non-conventional amino acid | Code |
| --- | --- | --- | --- |
| a-aminobutyric acid | Abu | 4-hydroxyproline | Hyp |
| α-amino-α-methyl-butyrate | Mgabu | L-pyroglutamic acid | pGlu |
| aminocyclopropane-carboxylate | Cpro | L-4-methoxytyrosine | MeY |
|  |  | L-N-methylalanine | Nmala |
| aminoisobutyric acid | Aib | L-N-methylarginine | Nmarg |
| aminonorbornyl-carboxylate | Norb | L-N-methylasparagine | Nmasn |
|  |  | L-N-methylaspartic acid | Nmasp |
| cyclohexylanine | Chexa | L-N-methylglutamine | Nmgln |
| cyclopentylanine | Cpen | L-N-methylglutamic acid | Nmglu |
| D-alanine | DAla | L-N-methylhistidine | Nmhis |
| D-arginine | DArg | L-N-methylisolleucine | Nmile |
| D-aspartic acid | DAsp | L-N-methylleucine | Nmleu |
| D-cysteine | DCys | L-N-methyllysine | Nmlys |
| D-glutamine | DGln | L-N-methylmethionine | Nmmet |
| D-glutamic acid | nGlu | L-N-methylnorleucine | Nmnle |
| D-histidine | DHis | L-N-methylnorvaline | Nmnva |
| D-isoleucine | DIle | L-N-methylornithine | Nmorn |
| D-leucine | DLeu | L-N-methylphenylalanine | Nmphe |
| D-lysine | DLys | L-N-methylproline | Nmpro |
| D-methionine | DMet | L-N-methylserine | Nmser |
| D-ornithine | DOrn | L-N-methylthreonine | Nmthr |
| D-phenylalanine | DPhe | L-N-methyltryptophan | Nmtrp |
| D-proline | DPro | L-N-methyltyrosine | Nmtyr |
| D-serine | DSer | L-N-methylvaline | Nmval |
| D-threonine | DThr | L-N-methylethylglycine | Nmetg |
| D-tryptophan | DTrp | L-N-methyl-t-butylglycine | Nmtbug |
| D-tyrosine | DTyr | L-norleucine | Nle |

TABLE 1-continued

| Non-conventional amino acid | Code | Non-conventional amino acid | Code |
| --- | --- | --- | --- |
| D-valine | DVal | L-norvaline | Nva |
| D-α-methylalanine | DMala | α-methyl-aminoisobutyrate | Maib |
| D-α-methylarginine | DMarg | α-methyl-γ-aminobutyrate | Mgabu |
| D-α-methyl-asparagine | DMasn | α-methylcyclohexylalanine | Mchexa |
| D-α-methylaspartate | DMasp | α-methylcyclopentylalanine | Mcpen |
| D-α-methylglutamine | DMgln | α-methyl-α-napthylalanine | Manap |
| D-α-methylhistidine | DMhis | α-methylpenicillamine | Mpen |
| D-α-methylisoleucine | DMile | N-(4-aminobutyl)glycine | Nglu |
| D-α-methylleucine | DMleu | N-(2-aminoethyl)glycine | Naeg |
| D-α-methyllysine | DMlys | N-(3-aminopropyl)glycine | Norn |
| D-α-methylmethionine | DMmet | N-amino-α-methylbutyrate | Nmaabu |
| D-α-methylornithine | DMorn | α-napthylalanine | Anap |
| D-α-methylphenylalanine | DMphe | N-benzylglycine | Nphe |
| D-α-methylproline | DMpro | N-(2-carbamylethyl)glycine | Ngln |
| D-α-methylserine | DMser | N-(carbamylmethyl)glycine | Nasn |
| D-α-methylthreonine | DMthr | N-(2-carboxyethyl)glycine | Nglu |
| D-α-methyltryptophan | DMtrp | N-(carboxymethyl)glycine | Nasp |
| D-α-methyltyrosine | DMty | N-cyclobutylglycine | Ncbut |
| D-α-methylvaline | DMval | N-cycloheptylglycine | Nchep |
| D-N-methylalanine | DNmala | N-cyclohexylglycine | Nchex |
| D-N-methylarginine | DNmarg | N-cyclodecylglycine | Ncdec |
| D-N-methyl-asparagine | DNmasn | N-cylcododecylglycine | Ncdod |
| D-N-methyl-aspartate | DNmasp | N-cyclooctylglycine | Ncoct |
| D-N-methylglutamine | DNmgln | N-cyclopropylglycine | Ncpro |
| D-N-methyl-glutamate | DNmglu | N-cycloundecylglycine | Ncund |
| D-N-methylhistidine | DNmhis | N-(2,2-diphenylethyl)-glycine | Nbhm |
| D-N-methyl-isoleucine | DNmile | N-(1-hydroxyethyl)glycine | Nthr |
| D-N-methylleucine | DNmleu | N-(3,3-diphenylpropyl)-glycine | Nbhe |
| D-N-methyllysine | DNmlys | N-(3-guanidinopropyl)-glycine | Narg |
| N-methylcyclohexylalanine | NMchexa | N-(hydroxyethyl)glycine | Nser |
| D-N-methylornithine | DNmorn | N-(imidazolylethyl)glycine | Nhis |
| D-N-methylmethionine | Dnmmet | N-(3-indolylyethyl)glycine | Nhtrp |
| N-methylglycine | Nala | N-methyl-γ-aminobutyrate | Nngabu |
| N-methylaminoisobutyrate | Nmaib | N-methylcyclopentylalanine | Nmcpen |
| N-(1-methylpropyl)-glycine | Nile | D-N-methylphenylalanine | DNmphe |
| N-(2-methylpropyl)-glycine | Nleu | D-N-methylproline | DNmpro |
| D-N-methyl-tryptophan | DNmtrp | D-N-methylserine | DNmser |
| D-N-methyltyrosine | DNmtyr | D-N-methylthreonine | DNmthr |
| D-N-methylvaline | DNmval | N-(1-methylethyl)glycine | Nval |
| γ-aminobutyric acid | Gabu | N-methylα-napthylalanine | Nmanap |
| L-t-butylglycine | Tbug | N-methylpenicillamine | Nmpen |
| L-ethylglycine | Etg | N-(p-hydroxyphenyl)-glycine | Nhtyr |
| L-homophenyl-alanine | Hphe | N-(thiomethyl)glycine | Ncys |
| L-α-methylarginine | Marg | penicillamine | Pen |
| L-α-methyl-asparagine | Masn | L-α-methylalanine | Mala |
| L-α-methylaspartate | Masp | L-α-methyl-t-butylglycine | Mtbug |
| L-α-methyl-glutamine | Mgln | L-methylethylglycine | Metg |
| L-α-methyl-glutamate | Mglu | L-α-methylhomophenyl-alanine | Mhphe |

TABLE 1-continued

| Non-conventional amino acid | Code | Non-conventional amino acid | Code |
|---|---|---|---|
| L-α-methylhistidine | Mhis | N-(2-methylthioethyl)-glycine | Nmet |
| L-α-methylisoleucine | Mile | L-α-methyllysine | Mlys |
| L-α-methylleucine | Mleu | L-α-methylnorleucine | Mnle |
| L-α-methylmethionine | Mmet | L-α-methylornithine | Morn |
| L-α-methylnorvaline | Mnva | L-α-methylproline | Mpro |
| L-α-methylphenylalanine | Mphe | L-α-methylthreonine | Mthr |
| L-α-methylserine | Mser | L-α-methyltyrosine | Mtyr |
| L-α-methyltryptophan | Mtrp | L-N-methylhomophenylalanine | Nmhphe |
| L-α-methylvaline | Mval | N-(N-(3,3-diphenylpropyl)carbamylmethylglycine | Nnbhe |
| N-(N-(2,2-diphenylethyl)carbamylmethylglycine | Nnbhm | O-methyl-L-serine | Omser |
| 1-carboxy-1-(2,2-diphenyl-ethyl-amino)cyclopropane | Nmbc | O-methyl-L-homoserine D-pyroglutamate | Omhser DpGlu |
| L-(-carboxyglutamic acid | Gla | | |

Particularly preferred sidechain modifications include the replacement of Tyr with MeY and/or replacement of Pro with Hyp.

These types of modifications, and others which involve more substantive sidechain modifications, may be important to stabilise the peptide if administered to an individual or used as a diagnostic reagent, or to improve solubility or bioavailability, or to provide other pharmacologies. For example it is possible to extend or contract sidechain length, or insert or remove functional groups to achieve these effects, eg by introduction of nitroxide donor groups.

The peptides of the present invention may be in the form of a salt, ester, amide or prodrug thereof. The χ-conotoxins of the present invention are typically amidated at the C-terminal, however compounds with a free carboxyl terminus or other modifications at the C-terminal are considered to be within the scope of the present invention. Preferably the peptides are amidated or have a free carboxyl at the C-terminal. The peptides according to the invention may be in the form of a salt or prodrug.

Examples of suitable salts include the chloride, acetate, lactate and glutamate salts. Conventional procedures for the preparation of suitable salts are well known in the art.

The peptides according to the present invention may also be in the form of prodrugs. Prodrugs are understood to include all derivatives of peptides according to the invention which are readily convertible in vivo into the required active peptide. Conventional procedures for the preparation of suitable prodrugs according to the invention are described in text books, such as "Design of Prodrugs" ed. H. Bundgaard, Elsevier, 1985.

The peptides of the present invention retain the Cys residues and characteristic disulphide bonding pattern of χ-conotoxin peptides.

The peptides can also be labelled and used to establish binding assays to identify new molecules that act at the same site. For example, a labelled peptide ligand could have tritium included or may have radio-active iodine or similar attached through a Tyr or other appropriate residue. The inhibition of binding of such labelled peptides to tissue homogenates or expressed transporters by compounds or mixtures would permit identification of new peptides active at this site, including peptides present in serum and nerve and muscle tissue of mammals, including human tissues. The assay will also allow identification of non-peptide molecules that also act at the same site as χ-conotoxin peptides, and that may have utility as orally active forms of these peptides. Labelled peptides will additionally permit autoradiographic studies to identify the location of the peptide binding across various tissues.

Contrary to what was proposed in WO00/20444 the χ-conotoxin peptides have been found to be non-competitive inhibitors in relation to noradrenaline, but competitive in relation to small molecules that also bind to the noradrenaline transporter, such as mazindol, cocaine and tricyclic antidepressants, such as desipramine.

Accordingly binding assays using labelled peptides of the present invention, preferably radio isotopically labelled, can be used to discover small molecules that could act as non competitive inhibitors of the noradrenaline transport through the noradrenaline transporter. Preferably this assay would be conducted in the presence of blocking concentrations of noradrenaline or related small molecules which do not overlap with the chi conopeptide binding site but which overlap with many small molecule inhibitors of the noradrenaline transporter (eg. tricyclic antidepressants).

The χ-conotoxins of the present invention may be prepared using standard peptide synthetic methods followed by oxidative disulfide bond formation. For example, the linear peptides may be synthesised by solid phase methodology using BOC chemistry, as described by Schnoltzer et al (1992). Following deprotection and cleavage from the solid support the reduced peptides are purified using preparative chromatography. The purified reduced peptides are oxidised in buffered systems, for example as described in the examples. The oxidised peptides can be purified using preparative chromatography.

References describing the synthesis of conotoxins include Sato et al, Lew et al and WO 91/07980.

The χ-conotoxins may also be prepared using recombinant DNA technology. A nucleotide sequence encoding the desired peptide sequence may be inserted into a suitable vector and protein expressed in an appropriate expression system. In some instances, further chemical modification of the expressed peptide may be appropriate, for example C-terminal amidation and conversion of an N-terminal glutamate residue to pyroglutamate residue. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

It may also be possible to prepare antiidiotypic antibodies using techniques known to the art. These antiidiotypic antibodies and their use as therapeutic agents represent a further aspect of the present invention.

The nucleic acid molecules may be in isolated form, or may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli*, *Bacillus* sp and *Pseudomonas* sp. Preferred eukaryotic cells include yeast, fungal, mammalian and insect cells.

Preferably, the gene portion of the genetic construct is operably linked to a promoter on the vector such that said promoter is capable of directing expression of the gene portion in an appropriate cell.

Chimeras of the χ-conotoxins of the present invention, with other conotoxins or additionally with other peptides or proteins, can be made to engineer the activity into other molecules, in some instances to produce a new molecule with extra functionality. For example, amino acids that bind to the N-type calcium channel can be combined with amino acids that inhibit NET to produce a peptide with activity at NET (using loop 1 residues of χ-conopeptides) and activity at the N-type calcium channel (using loop 2 of CVID), as in the N-/C-cylised CCSKLMYDCCGYKLG. Similarly, a cyclic peptide can be contrasted with loop 1 chi residues and a loop of amino acids having activity at opiate receptors, as in cCCRRQICCGYKLG. These chimeric peptides may be particularly useful as they possess pharmacologies that are additive or even synergistic, and are expected to be beneficial in the treatment of a wide range of pain syndromes that present in humans.

It should thus be understood that the terms conotoxin peptide or conotoxins are not limited to naturally occurring toxic peptides obtained from the genus *Conus* but rather simply indicates an initial source from which the peptides have been derived. Conotoxin peptides may be synthetically created, non-naturally occurring non-toxic peptide derivatives. Conopeptides is an alternative term interchangeable with conotoxin peptides.

A subset of these MrIA analogues may act at receptors in addition to the NET allowing synergistic or additional effects. Preferably these additional interactions synergise to enhance the antinociceptive effects. More preferably, these additional interactions occur at opioid receptors, opioid receptor like receptors, GPCRs of the MRG family, the NMDA receptors, glutamate receptors, the neurokinins, cyclooxygenase receptors, serotergenic receptors, adrenergic receptors, vanilloid receptors, benzodiazepines receptors, N-type calcium channel antagonists, neuronal nicotinic receptors, muscarinic acetylcholine capsaicin receptors, TNF-α, tetrodotoxin-resistant and tetrodotoxin-sensitive Na Channels, voltage-sensitive calcium channel and endothelian receptors.

Preferably the χ-conotoxin peptides according to the invention have 10 to 30 amino acids, more preferably 11 to 20.

The C-terminus may be extended by addition of a peptide "tail". In some cases the activity of the peptide can be improved by such modifications.

Examples of χ-conotoxin peptides according to the present invention include the following:

```
Xaa1 Gly Val Cys Cys Gly Tyr Lys Leu    SEQ ID NO. 4
Cys His Xaa3 Cys

Xaa1 Gly Val Cys Cys Gly Tyr Lys Leu    SEQ ID NO. 5
Cys His Xaa3 Xaa5

Xaa1 Gly Val Cys Cys Gly Xaa4 Lys Leu   SEQ ID NO. 6
Cys His Xaa3 Cys

Xaa1 Asn Gly Val Cys Cys Gly Xaa4 Lys   SEQ ID NO. 7
Leu Cys His Xaa3 Cys

Xaa1 Asn Gly Val Cys Cys Gly Tyr Lys    SEQ ID NO. 8
Leu Cys His Xaa3 Cys

Xaa1 Gly Val Cys Cys Gly Tyr Lys Leu    SEQ ID NO. 9
Cys His Xaa3 Cys —OH
```

In the sequences above, Xaa1 refers to pyroglutamic acid, Xaa3 refers to 4-hydroxyproline, Xaa4 refers to 4-methoxy tyrosine, Xaa5 (cys) refers to D-cysteine and —OH indicates a free acid C terminal.

Unless otherwise indicated the C-terminal of the peptide is preferably amidated.

Further examples of χ-conotoxin peptides according to the present invention include the following:

```
Xaa1 Gly Val Cys Cys Gly Tyr Lys Leu SEQ ID NO. 10
Cys His Xaa3 Cys —OH

Xaa1 Gly Val Cys Cys Gly Tyr Lys Leu SEQ ID NO. 11
Cys His Xaa3 Cys
```

In the sequences above, Xaa1 refers to D-pyroglutamic acid, Xaa3 refers to 4-hydroxyproline and —OH indicates a free acid C terminal.

The χ-conotoxin peptides according to the present invention are active in inhibiting neuronal noradrenaline transporter. Accordingly, the invention provides the use of the χ-conotoxin peptides as inhibitors of neuronal noradrenaline transporter, and in the treatment or prophylaxis of diseases or conditions in relation to which the inhibition of neuronal noradrenaline transporter is associated with effective treatment. Such activity in pharmacological agents is associated with activity in the prophylaxis or treatment of diseases or conditions of the urinary or cardiovascular systems, or mood disorders, or in the treatment or control of acute, chronic and/or neuropathic pain, migraine or inflammation.

Examples of the formulation and use of noradrenaline reuptake inhibitors in therapy can be found in Ardid, D et al., (1992) Fund. Clinical Pharmacology 6(2): 75-8; Yaksh, T. L. (1985) Pharmacology Biochemistry and Behaviour 22:845-858; Yaksh, T. L. & Takano, Y. (1992) J. Pharmacology & Experimental Therapeutics 261(2): 764-772; Yaksh, T. L. & Howe, J. R. (1982) J. Pharmacology & Experimental Therapeutics 220(2): 311-321; Howe, J. R. et al., (1983) J. Pharmacology & Experimental Therapeutics 224(3): 552-558; Solomon et al., (1989) J. Pharmacology & Experimental Therapeutics 251(1): 28-38; Fleetwood-Walker, S. M. et al., (1985) Brain Research 334:243-254; Takagi, H & Harima, A. (1996) European Neuropsychopharmacology 6, 43-47; Eisenach, J. C. et al (1998) Anesth Analg 87, 591-6; Dubner, R. & Hargreaves, K M (1989) Clin J Pain, 5 pS1-6; Max, M B (1992) N Engl J Med 326, p 1287-8; Atkinson, J H et al (1998) Pain 76, p 287-96; Mico, J. A. et al., (1997) European Neuropsychopharmacology 7, SI 62.

Accordingly the present invention provides a method for the treatment or prophylaxis of urinary or cardiovascular conditions or diseases or mood disorders or for the treatment or control of acute, chronic and/or neuropathic pain, migraine or inflammation including the step of administering to a mammal an effective amount of an isolated, synthetic or recombinant χ-conotoxin peptide having the ability to inhibit neuronal noradrenaline transporter, wherein said χ-conotoxin peptide comprises the following sequence of amino acids:

```
Xaa1 Xaa2 Gly Val Cys Cys Gly Tyr Lys SEQ ID NO. 3
Leu Cys His Pro Cys
``` where Xaa1 is a N-terminal pGlu or DpGlu residue; and

Xaa2 is Asn or a deletion;

or such a sequence in which one or more Cys is replaced with its corresponding D-amino acid and/or one or more amino acid residues other than Cys has undergone a side chain modification, or a salt or prodrug thereof.

In performing the method according to the present invention the administration of the χ-peptide may be performed in conjunction with other therapies useful in the treatment of the condition, disease or disorder. Accordingly the peptide may be administered substantially simultaneously or sequentially with other agents useful in the treatment of the conditions, diseases or disorders. Where the co-administration is simultaneous, the peptide may be formulated in a composition with one or more of the other agents. The co-administration of other agents can be performed via the same or different route to the route of administration for the χ-peptide. Where the method is for the treatment or control of acute, chronic and/or neuropathic pain or migraine, the peptide may be administered substantially simultaneously or sequentially with an analgesic agent selected from the group consisting of opioid analgesics, opioid receptor-like antagonists, GPCR antagonists of the MRG family, NMDA antagonists, substance P antagonists, COX 1 and COX 2 inhibitors, tricyclic antidepressants (TAC), selective serotonin reuptake inhibitors (SSRI), capsaicin receptor antagonists, anaesthetic agents, benzodiazepines, skeletal muscle relaxants, migraine therapeutic agents, anti-convulsants, anti-hypertensives, anti-arrhythmics, antihistamines, steroids, caffeine, N-type calcium channel antagonists, nicotinic receptor partial agonists and antagonists, vanilloid receptor antagonists and agonists, T-NF-α antagonists and antibodies, inhibitors of tetrodotoxin-sensitive Na Channels, P-type channel inhibitors, endothelian antagonists and botulinum toxin. The peptide may also be administered simultaneously with two or more other agents, for example mixtures of SSRIs and noradrenaline reuptake inhibitors.

Where the analgesic agent is an opioid receptor-like analgesic agent it is preferably selected from naltrexone and nalmefene; their pharmaceutically active salts and their optical isomers.

Where the analgesic agent is an opioid analgesic agent it is preferably selected from propoxyphene, meperidine, hydromorphone, hydrocodone, morphine, codeine and tramodol; their pharmaceutically active salts and their optical isomers.

Where the analgesic agent is an NMDA antagonist analgesic agent it is preferably selected from 2-piperdino-alkanol derivatives, dextromethorphan, eliprodil, and ifenprodil; their pharmaceutically active salts and their optical isomers.

Where the analgesic agent is a P antagonist analgesic agent it is preferably selected from 2-phenyl-piperidin-3-yl or 2-diphenylmethyl-1-azabicyclo[2.2.2]-octane-3-amine derivatives as described in U.S. Patent Application No. 2001/00336943 A1 (Coe et al.); their pharmaceutically active salts and their optical isomers.

Where the analgesic agent is a COX 2-inhibition analgesic agent it is preferably selected from rofecoxib and celecoxib; their pharmaceutically active salts and their optical isomers.

Where the analgesic agent is an anaesthetic analgesic agent it is preferably selected from nitrous oxide, halothane, lidocaine, etidocaine, ropivacaine, chloroprocaine, sarapin and bupivacaine; their pharmaceutically active salts and their optical isomers.

Where the analgesic agent is a benzodiazepine analgesic agent it is preferably selected from diazepam, chlordiazepoxide, alprazolam, lorazepam, midazolam, L-365260; their pharmaceutically active salts and their optical isomers.

Where the analgesic agent is a skeletal muscle relaxant analgesic agent it is preferably selected from flexeril, carisoprodol, robaxisal, norgesic and dantrium their pharmaceutically active salts and their optical isomers.

Where the analgesic agent is a migraine therapeutic agent it is preferably selected from elitriptan, sumatriptan, rizatriptan, zolmitriptan, and naratriptan their pharmaceutically active salts and their optical isomers.

Where the analgesic agent is an anticonvulsant analgesic agent it is preferably selected from gabapentin, pregabalin, carbamazepine, and topiramate and valproic acid their pharmaceutically active salts and their optical isomers.

Where the analgesic agent is a COX 1 inhibitor analgesic agent it is preferably selected from salycylic acid, acetominophen, diclofenac, piroxican indomethacin, ibuprofen, and naproxen their pharmaceutically active salts and their optical isomers.

Where the analgesic agent is a tricyclic antidepressant analgesic agent it is preferably selected from amitriptyline, desipramine, perphenazine, protriptyline, and tranylcypromine their pharmaceutically active salts and their optical isomers.

Where the analgesic agent is a SSRI analgesic agent it is preferably selected from tramadol and milnacipran; their pharmaceutically active salts and their optical isomers.

Where the analgesic agent is a mixture of SSRI and Noradrenaline reuptake inhibitors, the latter is preferably selected from reboxetine and atomoxetine; their pharmaceutically active salts and their optical isomers.

The analgesic agent may also be selected from adenosine, baclofen, clonidine, mexilitene, diphenyl-hydramine, hydroxysine, caffeine, prednisone, methylprednisone, decadron, paroxetine, sertraline, fluoxetine, Ziconotide®, and levodopa their pharmaceutically active salts and their optical isomers.

Where the analgesic agent is a TNF-α antagonist or antibody, the agent is preferably selected from etanercept, infliximab and thalidomide; their pharmaceutically active salts and their optical isomers.

Where the analgesic agent is an endothelian antagonist, the agent is preferably selected from bosentan and tesosentan; their pharmaceutically active salts and their optical isomers.

Where the analgesic agent is a vanilloid antagonist, the analgesic agent is preferably selected from ananamide, capsazepine, thiocarbamic acid derivatives (as described in WO02/16317 A1) and thiourea derivatives (as described in WO02/16318 A1); their pharmaceutically active salts and their optical isomers.

Where the analgesic agent is selected from nicotine receptor partial agonist it is preferably selected from 1,2,3,4,5,6-hexahydro-1,5-methano-pyrido[1,2-a][1,5]diazocin-8-one derivatives, diazatetracyclo[9.3.1.0.sup.2,10.0.sup.4,8]pentadeca-2(10),3,3-triene derivatives, 10-aza-tricyclo [6.3.1.0.sup.2,7]dodeca-2(7),3,5-triene derivatives, triazatetracyclo[9.3.1.0.sup.2,10.0.sup.4,8]pentadeca-2(10),3,5,8-tetraene derivatives, 5,8,14-triazatetracyclo[10.3.1.0.sup.2, 11.0.sup.4,9]hexadeca-2(11),3,5,7,9-pentaene derivatives, diazatetracyclo[9.3.1.0.sup.2,10.0.sup.4,8]pentadeca-2(10), 3,6,8-tetraene derivatives, 10-azatricyclo[6.3.1.0.sup.2,7] dodeca-2(7),3,5-triene derivatives, 5,7,14-triazatetracyclo [10.3.1.0.sup.2,10.0.sup.4,8]hexadeca-2(10),3,5,8-tetraene derivatives, 5,8,15-triazatetracyclo[11.3.1.0.sup.2, 11.0.sup.4,9]heptadeca-2(11),3,5,7,9-pentaene derivatives, 5,14-diazatetracyclo[10.3.1.0.sup.2,10.0.sup.4,8]hexadeca-2(10),3,5,8-tetraene derivatives, 11-azatricyclo [7.3.1.0.sup.2,7]trideca-2(7),3,5-triene derivatives, all of which are described in U.S. Patent Application No. 2001/00336943 A1 and their pharmaceutically acceptable salts and their optical isomers.

Examples of conditions associated with acute, chronic and/or neuropathic pain and inflammatory pain include soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhea, and labor pain; pain associated with nerve and root damage, such as pain associated with peripheral nerve disorders, for example, nerve entrapment and brachial plexus avulsions, amputation, peripheral neuropathies, neuralgia, tic douloureux, atypical facial pain, nerve root damage, pain and/or chronic nerve compression, and arachnoiditis; pain associated with carcinoma, often referred to as cancer pain; pain associated with AIDS, central nervous system pain, such as pain due to spinal cord or brain stem damage; low back pain; sciatica; headache, including migraine, acute or chronic tension headache, cluster headache, temporomandibular pain and maxillary sinus pain; ankylosing spondylitis, gout; post operative pain; phantom pains; diabetic neuropathy; shingles; and scar pain.

Examples of the formulation and use of conotoxin peptides in the treatment of pain can be found in WO9107980; U.S. Pat. No. 5,587,454 and WO9701351. These documents relate to omega conotoxins. Also see Bowersox S S, Gadbois T, Singh T, Pettus M, Wang Y X & Luther R R (1996) J Pharmacol Exp Ther, 279(3) pages 1243-9 which relates to conotoxin peptides that are selective N-type Voltage-sensitive calcium channel blockers and their use in the treatment of acute, persistent and neuropathic pain in rats.

Examples of diseases or conditions of the urinary system include urinary and fecal incontinence. Examples of cardiovascular diseases or conditions include arrhythmias of various origins and coronary heart failure. Examples of mood disorders include depression, anxiety, cravings, an addictive disorder and withdrawal syndrome, an adjustment disorder, age-associated learning and mental disorders, anorexia nervosa, apathy, attention-deficit disorders due to general medical conditions, attention-deficit hyperactivity disorder, bipolar disorder, bulimia nervosa, chronic fatigue syndrome, chronic or acute stress, conduct disorder, cyclothymic disorder, depression, dysthymic disorder, fibromyalgia and other somatoform disorders, generalised anxiety disorder, incontinence, inhalation disorders, intoxication disorders, mania, obesity, obsessive compulsive disorders and related spectrum disorders, oppositional defiant disorder, panic disorder, peripheral neuropathy, post-traumatic stress disorder, premenstrual dysphoric disorder, psychotic disorders, seasonal affective disorder, sleep disorders, social phobia, specific developmental disorders, selective serotonin reuptake inhibition (SSRI) "poop out" syndrome, and TIC disorders.

Examples of the use of selective noreprinephrine reuptake inhibitors in the treatment of diseases or conditions of the urinary system include Springer, J P., Kropp, B P & Thor K B (1994) J Urol 152(2), p 515-9 (relates to lower urinary tract); Penttila, O. et al (1975) Ann Clin Res (7), 32-6 (relates to treatment of ulcerative colitis) and Dinan, T G et al (1990) J Psychosom Res 34, p 575-80 (relates to treatment of irritable bowel syndrome).

Preferably the mammal is in need of such treatment although the peptide may be administered in a prophylactic sense.

The invention also provides a composition comprising an isolated, synthetic or recombinant χ-conotoxin peptide having the ability to inhibit neuronal noradrenaline transporter, wherein said χ-conotoxin peptide comprises the following sequence of amino acids:

```
Xaa1 Xaa2 Gly Val Cys Cys Gly Tyr Lys    SEQ ID NO. 3
Leu Cys His Pro Cys
``` where Xaa1 is a N-terminal pGlu or DpGlu residue; and

Xaa2 is Asn or a deletion;

or such a sequence in which one or more Cys is replaced with its corresponding D-amino acid and/or one or more amino acid residues other than Cys has undergone a side chain modification, or a salt or prodrug thereof, and a pharmaceutically acceptable carrier or diluent.

Preferably the composition is in the form of a pharmaceutical composition. The composition may also be other active agents useful in the treatment of the condition, disease or disorder present in the pharmaceutical composition.

There is also provided the use of an isolated, synthetic or recombinant χ-conotoxin peptide having the ability to inhibit neuronal noradrenaline transporter, wherein said χ-conotoxin peptide comprises the following sequence of amino acids:

```
Xaa1 Xaa2 Gly Val Cys Cys Gly Tyr Lys    SEQ ID NO. 3
Leu Cys His Pro Cys
``` where Xaa1 is a N-terminal pGlu or DpGlu residue; and

Xaa2 is Asn or a deletion;

or such a sequence in which one or more Cys is replaced with its corresponding D-amino acid and/or one or more amino acid residues other than Cys has undergone a side chain modification, or a salt or prodrug thereof, in the manufacture of a medicament for the treatment or prophylaxis of urinary or cardiovascular conditions or diseases, or mood disorders, or for the treatment or control of acute, chronic and/or neuropathic pain, migraine or inflammation.

It is also noted that noradrenaline transporter is expressed not only by nerve cells, but also by other tissues including the placenta, pulmonary endothelial cells and the uterus. The peptides according to the present invention may also be effective in inhibiting these noradrenaline transporters, and may be useful in treating conditions in which these transporters are implicated.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

For example the preferred route of administration for the treatment of urinary diseases is oral, topical, intranasal, intrarectal, intramucosal and intravenous. The same may be used for the treatment of pain and mode disorders, in addition to intrathecal administration. A method and formulations for use with conotoxin peptides in intrathecal administration is described in WO 9701351, the contents of which are incorporated by cross-reference.

The pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the peptides or modified peptides of the present invention using conventional approaches; Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin, E, reducing agents such as methionine or sulphite, and metal chelators such as EDTA.

Conventional approaches for the formulation of pharmaceutically active peptides are described in the following articles, the methodology of which are incorporated by reference: Ryan, 3 et al. (1986) Clin Pharmacol Ther (39), 40-2 (a clinical trial detailing the oral administration of the peptide nifalatide); Krames E. S. et al. (1986) Pain 24, 205-9 (describes the intrathecal delivery of a peptide); WO9614079A1 (which describes oral and rectal administration of formulations of the peptide cyclosporin); WO9640064A1 (which describes formulations for peptide stability); WO9805309A1 (describes peptide formulations—a pharmaceutical composition of cyclosporin for internal use and WO9802148A2 (which describes sustained release rectal and oral peptide formulations).

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged, absorption of the injectable compositions can be brought about by the use in the compositions, of agents delaying absorption, for example, aluminum monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various of the other ingredients such as these enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying a of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions, transdermal patches, sprays and gels, or compositions suitable for inhalation or intranasal delivery, for example solutions or dry powders.

Parenteral dosage forms are preferred, including those suitable for intravenous, subcutaneous, intrathecal, intracerebral or epidural delivery.

The composition may also be formulated for delivery via slow release implants, including implantable pumps, such as osmotic pumps.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 µg to about 2000 mg. Expressed in proportions, the active compound is generally present in from about 0.25 µg to about 200 mg/ml of carrier. In the case of compositions containing supplementary active ingredients, the dosages are determined by reference to the usual dose and manner of administration of the said ingredients.

The invention will now be described with reference to the accompanying drawings and examples, however it is to be understood that the particularity of the following description is not to supersede the generality of the preceding description of the invention.

Referring to the figures:

FIG. 1: Relief of tactile allodynia on the ipsilateral paw in the CCI rat using (a) SEQ ID NO. 4 (0.2-30 nM) over 6 hrs; (b) Morphine (3.5-50 nM) over 6 hrs; and (c) SEQ ID NO. 4 (1-3 nM) over 72 hrs.

Figure 2:
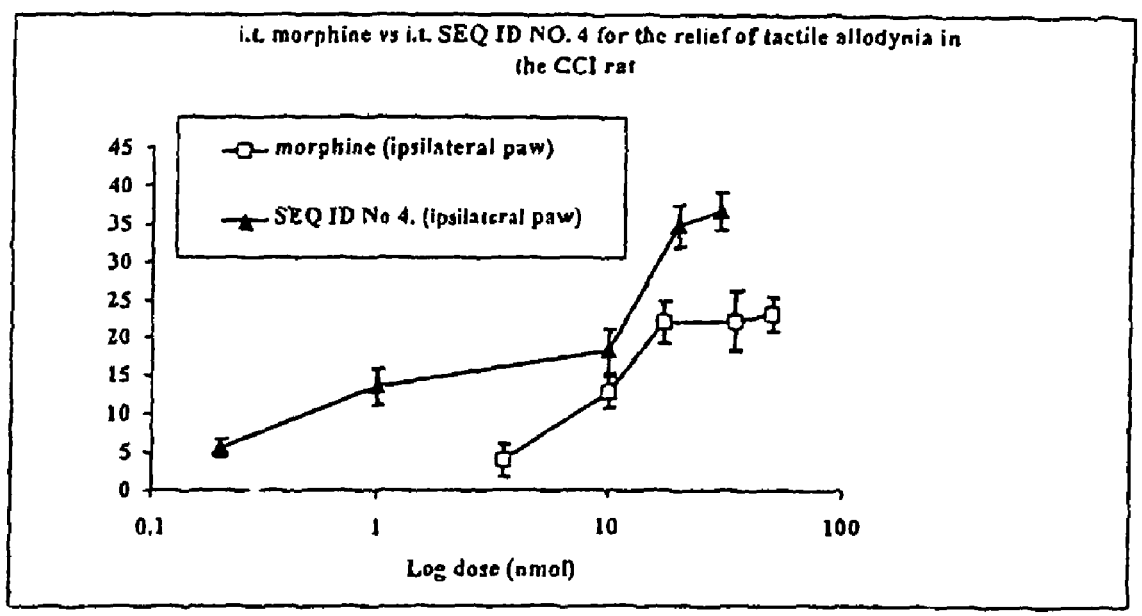

FIG. 2: i.t. Morphine vs i.t. 2174 for the relief of tactile allodynia on the ipsilateral paw in the CCI rat.

EXAMPLES

Example 1

Synthesis and Purification of MrIA (SEQ ID NO. 1), SEQ ID NO. 4 and Related MrIA Derivatives (a) Synthesis
(i) The peptide according to SEQ ID NO. 4 was assembled using F-moc chemistry methods based on the method of Scholzer et al. (Scholzer et al. Int. J. Prot. Pept. Res., 40, 180, (1992)) on Rink amide resin obtained from Polymer Laboratories. Conventional Trt/f-Bu sidechain protection was used throughout the chain assembly. The coupling efficiency was monitored using the ninhydrin test (Sarin et al., Anal. Biochem. 117, 145-157 (1981).
(ii) Other peptides were assembled using Boc-chemistry and conventional side chain protecting groups on a MBHA resin using (Sclinolzer et al, 1992). When this method is used cleavage is carried out using HF:scavengers (9:1) for 1 h at 0 to –10° C.

(b) Oxidation and Purification
(i) Oxidation of the pure reduced peptide assembled according to (a)(i) was carried out using an optimised buffer system (30 wt % DMSO/0.1M $NH_4HCO_3$, pH 6, 12 h) and the desired oxidised product having disulphide bond connectivity corresponding to that of MrIA was purified by using the RP-HPLC step (C-8 column with a gradient of from 10% B to 33% B over 40 min) to provide peptide with a purity greater than 99%.
(ii) Purification was achieved using one RP-HPLC step at both the reduced and oxidised peptide stage. This is in contrast with MrIA that requires a further purification step using an optimised chromatography program to remove a close eluting Asp-degradation impurity (Mw 1408.8, Asp, B-Asp).
(iii) The other peptides were oxidised and purified following procedures substantially the same as described above. In some syntheses the buffer system used was 30% isopropanol/0.11M $NH_4HCO_3$ pH 8.0 or a mixture of isopropanol/DMSO/0.1M $NH_4HCO_3$, pH8 8.

Example 2

Stability of Peptides Relative to MrIA

Methods

Peptides were dissolved at 1 mg/ml in 5 mM sodium acetate buffer/0.9% saline. The samples were stored at 37° C. and samples taken at intervals over a 31 day period. For comparison studies, a fresh sample of both peptides was made up from dry lyophilised powder stored at –20° C. at the same concentration in water just prior to evaluation. Samples were evaluated by RP-HPLC/MS using the optimised chromatography program described above and over a mass range of 300-1800 amu.

Results (a) Stability Using Different Buffers

The stability of the peptide of SEQ ID NO. 4 was measured in a range of buffer conditions at 37° C. The results, shown in Table 2, indicate that this peptide is stable under a range of conditions for extended periods of time.

TABLE 2

| Time | Acetate pH 4.5 | Acetate pH 5.0 | Acetate pH 5.5 | Lactate pH 4.5 | Lactate pH 5.0 | Lactate pH 5.5 |
|---|---|---|---|---|---|---|
| 6 days | 100 | 100 | 100 | 100 | 100 | 100 |
| 18 days | 100 | 100 | 100 | 100 | 100 | 100 |
| 31 days | 99.46 | 98.52 | 100 | 99.58 | 100 | 99.51 |

Graph 1. Stability of SEQ ID NO. 4 at 37EC after various times and in various buffers
Acetate Buffer = 5 mM Na acetate/acetic acid plus 0.9% saline
Lactate Buffer = 5 mM Na lactate/lactic acid plus 0.9% saline (b) Comparison of MrIA and SEQ ID NO. 4

The stability of the peptide of SEQ ID NO. 4 was also compared directly to the stability of MrIA at 37° C. The results shown in Table 3 highlights the greatly improved stability of the peptide of SEQ ID NO. 4. After 31 days more than 99% of the parent product is still present for the peptide of SEQ ID NO. 4. After the same time at 37° C. MrIA is significantly less stable with respect to its overall stability. Additionally, MrIA is almost completely converted to the degradation products (Asn to Asp and B-Asp, JBC, Vol 286 (33), pp 22549-22556, 1991 Tyler-Cross, R and Schirch, V.) after 31 days.

TABLE 3

Stability of MrIA and SEQ ID NO. 4 at 37° C. over time in 5 mM Na acetate/acetic acid plus 0.9% saline pH 5.5

| Sample | % purity | |
|---|---|---|
| | 6 days | 31 days |
| SEQ ID NO. 4 (fresh) | 100.00 | 100.00 |
| SEQ ID NO. 4 | 100.00 | 100.00 |

TABLE 3-continued

Stability of MrIA and SEQ ID NO. 4 at 37° C. over time in 5 mM
Na acetate/acetic acid plus 0.9% saline pH 5.5

| Sample | % purity | |
|---|---|---|
| | 6 days | 31 days |
| MrIA (fresh) | 99.77 | 9.77 |
| MrIA | 94.04* | 93.30† |

*contains a mixture of MrIA and Asp1MrIA;
†contains predominantly Asp1MrIA.

Example 3

The binding activity at the human noradrenaline transporter (hNET) and noradrenaline (NA) uptake were measured for several peptides according to the invention, as well as for MrIA and other peptides not according to the invention.

(i) hNET Radioligand Binding Assay

The ability of χ-conotoxins to act as inhibitors of the human noradrenaline transporter (hNET) can be measured by their competitive inhibition of $^3$H-nisoxetine from membrane prepared from COS-7 mammalian cells expressing hNET. Similar results are observed with other 3H-small molecules, such as mazindol.

COS-7 cells (ATCC) grown in 150 mm dishes containing DMEM and 10% serum were transiently transfected with plasmid DNA encoding mammalian (human) NET (Percy et al 1999, Br J Pharmacol 128: 774-780) using metafectene reagent (Biontex). Cells were harvested 48 hrs post transfection cells were: scraped, washed, homogenized and centrifuged using TEM buffer. For each 150 mm dish membrane was resuspended in 500 μL TEM with 10% glycerol. BCA protein estimates were performed giving≈6 μg/μL. 1 μL membrane+49 μL assay buffer was used per well in the assay (assay buffer is 20 mM TrisHCl pH 7.4, 15 mM NaCl, 0.1 mM EDTA, 0.1 mM EGTA, 0.1% BSA). Total assay volume was 150 μL and each data point performed in triplicate. Peptides at various concentrations ($10^{-4}$ to $10^{-11}$M) or control ligand (nisoxetine) were added to the assay plate followed by 4.3 nM $^3$H-nisoxetine (Perkin Elmer cat # NET1084). Finally the membrane was added and the assay was incubated for 1 hr at RT after which the reaction was filtered onto GF filtermats B (Perkin Elmer cat #: 1450-521) pretreated with 0.6% PEI using a Tomtec cell harvester and washed 3 times using wash buffer (20 mM HEPES pH 7.4, 125 mM NaCl @ 4° C.). Filtermats were then dried, placed in a filter bag, 9 mLs betaplate scintillant (Perkin Elmer cat # 1205-440) added and filtermats counted on a Wallac MicroBeta instrument. Each data point was performed in triplicate and the results summarised in Table 4 are from n≧3 experiments.

(ii) NA Uptake Assay

The ability of χ-conotoxins to act as inhibitors of the human noradrenaline transporter (hNET) can be measured by their non-competitive inhibition of the function of noradrenaline transporter to transport $^3$H-noradrenaline into COS7 mammalian cells expressing hNET.

COS-7 cells (ATCC) grown in 24 well plates containing DMEM and 10% serum were transiently transfected with plasmid DNA encoding the mammalian (human) NET using metafectene reagent (Biontex). Uptake assays were performed at RT 48 hrs post transfection in transport buffer containing 125 mM NaCl, 4.8 mM KCl, 1.2 mM $MgSO_4$, 1.2 mM $KH_2PO_4$, 1.3 mM $CaCl_2$, 25 mM HEPES pH7.4, 5.55 mM glucose, 1.02 mM ascorbic acid, 10 μM U-0521 and 100 μM pargyline. Total assay volume was 250 μL. Cells was 3 times with warm PBS followed by the addition of assay buffer. To which was added control or competing ligand at various concentrations ($10^{-4}$ to $10^{-11}$M). Assay was incubated for 20 mins after which 100 nM $^3$H-noradrenaline was added and allowed to incubate for 10 mins. Assay stopped by removal and washing with cold PBS. Cells lysed with 500 μL 0.1% SDS, 0.1N NaCl. 100 μL aliquots taken and added to flexible 96 well plate (for the counter) to which supermix scintillant was added (100 μL), mixed well and counted for 3 mins per well. Each data point was performed in triplicate and the results, summarised in Table 4, are from n≧3 experiments.

The results are shown below in Table 4. In the table "h", "c" and "u" refer to D-histidine, D-cysteine and D-pyroglutamate respectively, O refers to 4-hydroxy proline, MeY refers to 4-methoxy tyrosine and U refers to pyroglutamate, and —OH indicates that there is a free acid C terminal.

TABLE 4

| χ-Peptide | Sequence | Ay log $IC_{50}$ for displacement of $^3$H-nisoxetine from hNET | Ay log $IC_{50}$ for for inhibition of $^3$H-NA through hNET |
|---|---|---|---|
| SEQ ID NO. 1 | N G V C C G Y K L C H O C | −5.14 | −6.30 |
| SEQ ID NO. 4 | U G V C C G Y K L C H O C | −5.57 | −6.48 |
| SEQ ID NO. 12 (comparative) | U G V C C G Y K L C h O C | −4.22 | −4.15 |
| SEQ ID NO. 5 | U G V C C G Y K L C H O c | −5.38 | −6.24 |
| SEQ ID NO. 6 | U G V C C G MeY K L C H O C | −5.94 | −6.67 |
| SEQ ID NO. 7 | U N G V C C G MeY K L C H O C | −5.64 | −6.58 |
| SEQ ID NO. 8 | U N G V C C G Y K L C H O C | −5.33 | −6.12 |
| SEQ ID NO. 9 | U G V C C G Y K L C H O C —OH | −5.08 | — |
| SEQ ID NO. 10 | u G V C C G Y K L C H O C —OH | −5.16 | — |
| SEQ ID NO. 11 | u G V C C G Y K L C H O C | −5.56 | — |

— indicates not tested

Example 4

Comparison of the Antinociceptive Effects of SEQ ID NO. 4, MrIA and Morphine in a Rat Model of Neuropathic Pain Methods Animals Adult male Sprague-Dawley rats were purchased from the Animal Resources Centre (ARC), Perth, Australia, and the Herston Medical Research Centre, The University of Queensland. Rats were housed in a temperature controlled environment (21±2° C.) with a 12 h/12 h light/dark cycle. Food and water were available ad libitum. Ethical approval for this study was obtained from the Animal Experimentation Ethics Committee of The University of Queensland.

Reagents and Materials

Isoflurane (Forthane®) was obtained from Abbott Australasia Pty Ltd (Sydney, Australia). Sodium benzylpenicillin vials (600 mg) were purchased from CSL Ltd (Melbourne; Australia). Normal saline ampoules were obtained from Delta West Pty Ltd (Perth, Australia) and heparinised saline (50 IU/5 ml) was purchased from Astra Pharmaceuticals Pty Ltd (Sydney, Australia). Single lumen polyethylene tubing (I.D. 0.2 mm, O.D. 0.6 mm) was purchased from Auburn Plastics and Engineering Pty Ltd (Sydney, Australia). Sterile siliconized silk sutures (Dysilk™) were obtained from Dynek Pty Ltd (Adelaide, South Australia) and Michel clips were purchased from Medical and Surgical Requisites Pty Ltd (Brisbane, Australia).

Chronic Constriction Injury (CCI) of the Sciatic Nerve

Rats were anaesthetised with ketamine (80 mg/kg) and xylazine (8 mg/kg) administered by intraperitoneal injection, and a chronic constriction injury (CCI) of the sciatic nerve was produced according to the method of Bennett and Xie (1988). Briefly, the left common sciatic nerve was exposed at mid-thigh level by blunt dissection through the biceps femoris. Proximal to the trifurcation, ≈10 mm of nerve was freed of adhering tissue and four loose ligatures (3.0 silk) were tied around the sciatic nerve (≈1 mm apart). The incision was closed in layers. After surgery, rats received benzylpenicillin (60 mg s.c.) to prevent infection and were kept warm during surgical recovery. Rats were housed singly for 14 days prior to opioid or vehicle administration. Rats were inspected daily from the time of CCI-surgery with regard to posture of the affected hindpaw, exploring behaviour, body weight and water intake, and any signs of autotomy. Early signs of autotomy were seen in one rat (gnawing of claw tips and some surrounding tissue on the ipsalteral hindpaw) and this animal was promptly euthanased.

Intrathecal Catheter Insertion

Ten to eleven days post CCI-surgery or in untreated controls, rats were deeply anaesthetised with a mixture of ketamine (80 mg kg$^{-1}$) and xylazine (8 mg/kg) administered as a single intraperitoneal (i.p.) injection. Prior to surgery, the back and neck regions of the rat were shaved and the skin cleansed with betadine surgical scrub. The rat was then placed in a prone position and the L6 lumbar vertebra was located by palpation of the tuber sacrales of the os ileum (Hebel & Stromberg 1976). A 6 cm incision was made in the midline of the back, 3 cm caudal and 3 cm cephalad to L6. A subcutaneous pocket (for the intrathecal catheter) was formed by blunt dissection with scissors on both sides of the incision. The fascia covering the superficial muscles of the back were cut in a 5 mm V-shaped incision that encompassed L5. Additional 5 mm caudal incisions were made parallel to L6. The fascia was then retracted and the lumbar muscles surrounding the base of L5 and L6 were removed, as was the m. interspinalis between the spinous processes of L5-L6.

Following removal of the L6 spinous processes with rongeurs, the soft tissue beneath the L5 iliac arch was removed, exposing the dura mater. The dural membrane was pierced with a 23 G needle, releasing clear CSF. A polyethylene catheter (O.D. 0.6 mm, I.D. 0.2 mm; 20 cm in length) pre-filled with saline, was carefully advanced a distance of 1 cm into the intrathecal space and a small volume of saline (20 µL) was administered through the catheter. If leakage of saline around the catheter was observed, the rat was excluded from further experimentation. After successful completion of the 'leak test', the intrathecal (i.t.) catheter was fixed with dental cement onto the surrounding muscle ~2 cm from L5, exteriorised through a subcutaneous (s.c.) tunnel to a small incision at the base of the neck and sutured in position. After suturing of the lumbar muscles and skin, rats received benzylpenicillin (50000 IU i.p.) and enrofloxacin (5 mg·kg$^{-1}$ s.c.) to prevent infection and were kept warm during recovery from anaesthesia. Following completion of the surgery, rats were housed singly for a recovery period of 3-4 days prior to i.t. drug administration. On the day following surgery, the local anaesthetic, lignocaine (2%, 20 µL) was administered via the i.t. catheter. If-complete paralysis of both hind legs was not observed, rats were excluded from further experimentation.

Drugs Administered

SEQ ID NO. 4 was prepared in 5 mM sodium acetate buffer at pH 5.5 at delivered to rats in a single bolus dose of 0.2-30 nmoles. Stock solutions of the peptides were quantified relative to an amino acid analysed stock solution by reversed phase HPLC with u.v. detection at Xenome Ltd. Morphine HCl powder was purchased from the Royal Brisbane Hospital Central Pharmacy (Herston, Queensland) and dissolved in normal saline to prepare a stock concentration of 10 µg/10 µl (morphine base). Each rat received 3.5-50 nmol (10-15 µl) of morphine. All dilutions were made with normal saline. All i.t. injections were followed by a saline flush (20 µL) to ensure complete peptide delivery into the intrathecal space.

Storage of Stock Solutions

Aliquots (10 µL) of stock solutions were stored at −20° C. prior to use for animal experimentation. Immediately prior to experimentation, aliquots of the relevant compound were thawed at room temperature and then diluted to the required concentration with sterile saline to achieve the desired final concentration for subsequent i.t. Unused portions were discarded to waste to ensure that compounds only underwent one freeze-thaw cycle.

Intrathecal Drug Dosing

On day 14 post-CCI surgery, individual groups of drug-naïve-CCI rats received an i.t. bolus injection of SEQ ID NO. 4 morphine or saline in a volume of 10-15 µL Antinociception was assessed using von Frey filaments until responses returned to baseline.

Assessment of Antinociception: CCI Rats Using von Frey Filaments

Tactile allodynia, the distinguishing feature of neuropathic pain, was quantified using von Frey filaments which were used to apply a non-noxious mechanical stimulus (light pressure) to the hindpaw. Rats were transferred to wire mesh testing cages (20 cm×20 cm×20 cm) and allowed to acclimatize for 10 min. Von Frey filaments were used to determine the lowest mechanical threshold required for a brisk paw withdrawal reflex. Briefly, starting with the von Frey filament that produced the lowest force, the filament was applied to the plantar surface of the hindpaw until the filament buckled slightly. Absence of a response after 5 s prompted use of the next filament of increasing weight. Filaments used produced a buckling weight of 2, 4, 6, 8, 10, 12, 14, 16, 18 and 20 g and these were calibrated regularly. A score of 20 g was given to animals that did not respond to any of the von Frey filaments. Paw withdrawal thresholds (g) were converted to area under the curve (AUCh). The maximum response on the ipsilateral side was 45 AUCh Verification of Correct i.t. Catheter Placement At the completion of each experiment, malachite green dye (30 µL) was injected via the i.t. catheter whilst rats were lightly anaesthetised with $O_2:CO_2$ (50%:50%). Thirty seconds later, rats were decapitated and the spinal column was exposed surgically. Data from rats where there was evidence of subcutaneous dye leakage at the site where the catheter entered the back muscles above L6 or failure of the dye to distribute at least 3-4 cm along the spinal cord, were excluded from the analysis.

Data Analysis

The areas under the degree of antinociception versus time curves (AUC values) for each of the peptides were calculated from time=0 to 3 h. Dose-response curves for each of the peptides were constructed by plotting AUC values versus the i.t. peptide dose (expressed in nmol per rat).

Results

Both SEQ ID NO. 4 (FIG. 1A,C) and morphine (FIG. 1B) produced antinociceptive effects in a rat model of neuropathic pain when injected as a single bolus dose by the intrathecal route (i.t.). These effects were dose-dependent (FIG. 2). While both compounds produced similarly mild side-effects, SEQ ID NO. 4 produced antinociceptive effects that were greater in both extent and duration using lower doses of compound (FIG. 1). Surprisingly, SEQ ID NO. 4 at close to a maximum efficacious dose produced antinociceptive effects that lasted for 2 days. In contrast, morphine at a maximum efficacious i.t. dose produced effects that lasted for only 3 hr. Given that SEQ ID NO. 4 produces moderate antinociceptive effects at 1 nmole and relatively mild side effects at 30 nmole that were not dose limiting, SEQ ID NO. 4 has a therapeutic window of at least 30-fold. The antinociceptive effects of both morphine and SEQ ID NO. 4 were selective for the ipsilateral over the contralateral paw.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention claimed is:

1. An isolated, synthetic or recombinant χ-conotoxin peptide comprising the following sequence of amino acids:

Xaa1 Xaa2 Gly Val Cys Cys Gly Tyr Lys Leu Cys His Pro Cys SEQ ID NO. 3 where Xaa1 is a N-terminal pyroglutamate (pGlu) or D-pyroglutamate (DpGlu) residue; and Xaa2 is Asn or a deletion; optionally one or more Cys is replaced with its corresponding D-amino acid, optionally Pro has been replaced with 4-hydroxyproline, and optionally Tyr is substituted with 4-methoxy tyrosine; or a salt or amide thereof.

2. The peptide according to claim 1 consisting of the following sequence of amino acids:

Xaa1 Xaa2 Gly Val Cys Cys Gly Tyr Lys Leu Cys His Pro Cys SEQ ID NO. 3 where Xaa1 is a N-terminal pyroglutamate (pGlu) or D-pyroglutamate (DpGlu) residue; and Xaa2 is Asn or a deletion; optionally one or more Cys is replaced with its corresponding D-amino acid, optionally Pro has been replaced with 4-hydroxyproline, and optionally Tyr is substituted with 4-methoxy tyrosine; or a salt or amide thereof.

3. The peptide according to claim 1 wherein Pro has been replaced with 4-hydroxyproline.

4. The peptide according to claim 1 having the following sequence of amino acids

```
Xaa1 Gly Val Cys Cys Gly Tyr Lys Leu      SEQ ID NO. 4
Cys His Xaa3 Cys

Xaa1 Gly Val Cys Cys Gly Tyr Lys Leu      SEQ ID NO. 5
Cys His Xaa3 Xaa5

Xaa1 Gly Val Cys Cys Gly Xaa4 Lys Leu     SEQ ID NO. 6
Cys His Xaa3 Cys

Xaa1 Asn Gly Val Cys Cys Gly Xaa4 Lys     SEQ ID NO. 7
Leu Cys His Xaa3 Cys

Xaa1 Asn Gly Val Cys Cys Gly Tyr Lys      SEQ ID NO. 8
Leu Cys His Xaa3 Cys

Xaa1 Gly Val Cys Cys Gly Tyr Lys Leu      SEQ ID NO. 9
Cys His Xaa3 Cys —OH
``` or where Xaa1 is N-terminal pGlu, Xaa3 is 4-hydroxyproline, Xaa4 is 4-methoxy tyrosine, Xaa5 is D-cysteine and —OH indicates a free acid C terminal.

5. The peptide according to claim 1 having the following sequence of amino acids

```
Xaa1 Gly Val Cys Cys Gly Tyr Lys Leu SEQ ID NO. 10
Cys His Xaa3 Cys —OH

Xaa1 Gly Val Cys Cys Gly Tyr Lys Leu SEQ ID NO. 11
Cys His Xaa3 Cys
``` where Xaa1 is DpGlu, Xaa3 is 4-hydroxyproline and —OH indicates a free acid C terminal.

6. A composition comprising the peptide of any one of claims 1 to 5 together with pharmaceutically acceptable carrier or diluent.

7. The composition of claim 6 further comprising one or more other active agents.

8. An isolated, synthetic or recombinant χ-conotoxin peptide or a salt, ester or amide thereof, wherein said peptide comprises the following amino acid sequence:

```
                                    (SEQ ID NO: 4)
pGlu Gly Val Cys Cys Gly Tyr Lys Leu Cys His
Hyp Cys.
```

9. An isolated, synthetic or recombinant amidated χ-conotoxin peptide, wherein said peptide comprises the following amino acid sequence:

```
                                    (SEQ ID NO: 4)
pGlu Gly Val Cys Cys Gly Tyr Lys Leu Cys His
Hyp Cys,
``` and wherein the C-terminal Cys residue is amidated.

10. A method for the treatment or control of acute, chronic and/or neuropathic pain, migraine or inflammatory pain in a mammal comprising administering to the mammal an effective amount of an isolated, synthetic or recombinant χ-conotoxin peptide of any one of claim 1-5 or 8-9.

11. The method of claim 10, wherein the peptide is administered substantially simultaneously or sequentially with other agents useful in the treatment of said pain or migraine.

12. The method of claim 10, wherein said method is for the treatment and control of neuropathic pain.

13. The method of claim 12, wherein the neuropathic pain is associated with surgery (post operative pain), gut, cancer, diabetic, phantom limb, or nerve damage.

* * * * *

UNITED STATES PATENT AND TRADEMARK OFFICE
CERTIFICATE OF CORRECTION

| | | |
|---|---|---|
| PATENT NO. | : 7,851,444 B2 | Page 1 of 1 |
| APPLICATION NO. | : 10/537704 | |
| DATED | : December 14, 2010 | |
| INVENTOR(S) | : Richard J. Lewis et al. | |

It is certified that error appears in the above-identified patent and that said Letters Patent is hereby corrected as shown below:

On the title page item (73) should read:

Assignee: Xenome Ltd., Queensland (AU)

Signed and Sealed this

First Day of February, 2011

David J. Kappos
*Director of the United States Patent and Trademark Office*